United States Patent
Sudo et al.

(10) Patent No.: US 11,439,721 B2
(45) Date of Patent: Sep. 13, 2022

(54) ALDEHYDE SCAVENGER AND METHOD FOR REMOVING ALDEHYDES

(71) Applicants: TOSOH CORPORATION, Shunan (JP); Sagami Chemical Research Institute, Ayase (JP)

(72) Inventors: Yukinori Sudo, Shunan (JP); Takahiro Masuda, Shunan (JP); Osamu Kobayashi, Ayase (JP); Takuri Ozaki, Ayase (JP); Kenji Hirai, Ayase (JP)

(73) Assignees: TOSOH CORPORATION, Shunan (JP); Sagami Chemical Research Institute, Ayase (JP)

( * ) Notice: Subject to any disclaimer, the term of this patent is extended or adjusted under 35 U.S.C. 154(b) by 368 days.

(21) Appl. No.: 16/466,232

(22) PCT Filed: Dec. 27, 2017

(86) PCT No.: PCT/JP2017/047018
§ 371 (c)(1),
(2) Date: Jun. 3, 2019

(87) PCT Pub. No.: WO2018/124208
PCT Pub. Date: Jul. 5, 2018

(65) Prior Publication Data
US 2020/0061225 A1    Feb. 27, 2020

(30) Foreign Application Priority Data

Dec. 28, 2016 (JP) .............................. JP2016-254724
Dec. 28, 2016 (JP) .............................. JP2016-254725
(Continued)

(51) Int. Cl.
*A61L 9/014* (2006.01)
*B01D 53/02* (2006.01)
*B01J 20/32* (2006.01)

(52) U.S. Cl.
CPC ............. *A61L 9/014* (2013.01); *B01D 53/02* (2013.01); *B01J 20/3204* (2013.01);
(Continued)

(58) Field of Classification Search
CPC ... A61L 9/014; B01D 53/02; B01D 2257/708; B01D 2258/06; B01D 2259/4508; B01D 2259/4566; B01J 20/3204; B01J 20/3251
(Continued)

(56) References Cited

U.S. PATENT DOCUMENTS 3,493,467 A    2/1970 Drell et al.
5,112,741 A    5/1992 Palmer et al.
(Continued)

FOREIGN PATENT DOCUMENTS

JP    4-358536 A    12/1992
JP    11-4879 A    1/1999
(Continued)

OTHER PUBLICATIONS

International Search Report dated Feb. 27, 2018 in PCT/JP2017/047018 filed Dec. 27, 2017.
(Continued)

*Primary Examiner* — Anita Nassiri-Motlagh
(74) *Attorney, Agent, or Firm* — Oblon, McClelland, Maier & Neustadt, L.L.P.

(57) ABSTRACT

To provide an aldehyde scavenger and a method for removing aldehydes by using the same, for quickly and continuously capturing aldehydes. An aldehyde scavenger comprising at least one O-substituted hydroxylamine or at least one chemically acceptable salt thereof, is used against an aldehyde generation source.

16 Claims, 3 Drawing Sheets

(30) Foreign Application Priority Data

Dec. 21, 2017 (JP) .............................. JP2017-245500
Dec. 21, 2017 (JP) .............................. JP2017-245501

(52) U.S. Cl.
CPC ..... B01J 20/3251 (2013.01); *B01D 2257/708* (2013.01); *B01D 2258/06* (2013.01); *B01D 2259/4508* (2013.01); *B01D 2259/4566* (2013.01)

(58) Field of Classification Search
USPC ............................................................ 422/4
See application file for complete search history.

(56) References Cited

U.S. PATENT DOCUMENTS

| | | | |
|---|---|---|---|
| 5,206,204 | A | 4/1993 | Tsutsumi et al. |
| 5,278,225 | A | 1/1994 | Kohlhammer et al. |
| 7,790,467 | B1 | 9/2010 | Massick |
| 2006/0275913 | A1 | 12/2006 | Kitasaka et al. |

FOREIGN PATENT DOCUMENTS

| | | |
|---|---|---|
| JP | 2011-173070 A | 9/2011 |
| JP | 2012-120708 A | 6/2012 |
| JP | 2012-224608 A | 11/2012 |
| WO | WO 01/81367 A2 | 11/2001 |

OTHER PUBLICATIONS

Harumitsu Nishikawa, et al., "Properties of Apatite Absorbent Modified with O-methylhydroxylamine for Gaseous Aldehyde," Journal of the Society of Inorganic Materials, Japan, vol. 18, No. 353, Jul. 2011, 7 Pages.

Tamás et al., "The Mass Spectra of Some α-Aminooxy Acids", Organic Mass Spectrometry, 1974, vol. 9, pp. 672 to 678.

Amrhein et al., "α-aminooxy-β-phenylpropionic acid—a potent inhibitor of L-phenylalanine ammonia-lyase in vitro and in vivo", Plant Science Letters, vol. 8, 1977, pp. 313 to 317.

STN Registry database, CAS 1784926-91-5, 2022, 1 page.

STN Registry database, CAS 2211-12-3, 2022, 1 page.

ALDEHYDE SCAVENGER AND METHOD FOR REMOVING ALDEHYDES

TECHNICAL FIELD

The present invention relates to a scavenger of aldehydes, and a method for removing aldehydes by using it.

BACKGROUND ART

Aldehydes such as acetaldehyde and formaldehyde are typical odorants in the living environment, and they cause unpleasant odors even at low concentrations since their odor threshold is extremely low. These aldehydes are known to be generated from a synthetic resin, plywood, cigarette smoke, etc. in an indoor or an automobile, to cause a sick house syndrome or sick car syndrome. In addition, these aldehydes are suspected to be also carcinogenic, and if people are routinely exposed to these, there is a risk of harm to health. Therefore, as the indoor concentration guideline values by Ministry of Health, Labor and Welfare, acetaldehyde is defined to be at most 0.03 ppm, and formaldehyde is defined to be at most 0.08 ppm. Therefore, a means to quickly and continuously removing aldehydes is desired.

Since lower aldehydes such as acetaldehyde and formaldehyde have low boiling points, the capture efficiency is low by an inorganic porous material such as silica gel or activated carbon, which is widely used as a deodorant. Therefore, a method of capturing aldehydes by letting them chemically react with an aldehyde scavenger consisting of a hydrazine derivative, an amine, an amino acid or a urea derivative, has been proposed (e.g., see Patent Documents 1 to 3).

However, the methods disclosed in these Patent Documents 1 to 3 had problems such that the capture efficiency is insufficient, the scavengers themselves are odor sources, or even if aldehydes have been once captured, the aldehydes are likely to be released again as the time passes. Also, in a case where the aldehyde scavengers disclosed in these Patent Documents 1 to 3 are used in a dwelling or in an automobile for the purpose of preventing a sick house syndrome or a sick car syndrome, these locations become a high temperature in summer or the like, whereby there has been a problem that the performance tends to decrease.

PRIOR ART DOCUMENTS

Patent Documents

Patent Document 1: JP-A-H4-358536
Patent Document 2: JP-A-H11-4879
Patent Document 3: JP-A-2012-120708

DISCLOSURE OF INVENTION

Technical Problem

The present invention has been made in view of the above background art, and it is an object of the present invention to provide an aldehyde scavenger and a method for removing aldehydes, for quickly and continuously capturing aldehydes.

Solution to Problem

The present inventors have made intensive studies for solving the above problem, and as a result, they have found that an aldehyde scavenger containing a specific O-substituted hydroxylamine or a chemically acceptable salt thereof captures aldehydes quickly and continuously, and thus have accomplished the present invention.

That is, the present invention has the following gist.

[1] An aldehyde scavenger characterized by comprising at least one O-substituted hydroxylamine, or at least one chemically acceptable salt thereof.

[2] The aldehyde scavenger according to [1], wherein the O-substituted hydroxylamine is an O-substituted mono hydroxylamine.

[3] The aldehyde scavenger according to [2], wherein the O-substituted mono hydroxylamine is an O-substituted mono hydroxylamine represented by the following formula (1):

$$R^1-ONH_2 \qquad (1)$$

in the formula (1), $R^1$ is a $C_{1-18}$ linear, branched or cyclic alkyl group which may be substituted, at an chemically acceptable optional position, by at least one substituent selected from the group consisting of a halogen atom;
a $C_{1-6}$ alkyloxy group;
a $C_{1-6}$ haloalkyl group;
a $C_{1-6}$ haloalkyloxy group;
a carboxy group;
a hydroxy group;
a mercapto group;
a cyano group;
a nitro group;
a $C_{6-14}$ aryl group which may be substituted by a halogen atom, a $C_{1-6}$ alkyl group, a $C_{1-6}$ alkyloxy group, a $C_{1-6}$ haloalkyl group, a $C_{1-6}$ haloalkyloxy group, a carboxy group, a hydroxy group, a mercapto group, a cyano group or a nitro group;
a $C_{4-14}$ heteroaryl group which may be substituted by a halogen atom, a $C_{1-6}$ alkyl group, a $C_{1-6}$ alkyloxy group, a $C_{1-6}$ haloalkyl group, a $C_{1-6}$ haloalkyloxy group, a carboxy group, a hydroxy group, a mercapto group, a cyano group or a nitro group;
an alkoxycarbonyl group represented by the following formula (2); and
a carbamoyl group represented by the following formula (3):

in the formula (2), $R^2$ is a $C_{1-18}$ linear, branched or cyclic alkyl group which may be substituted, at a chemically acceptable optional position, by at least one substituent selected from the group consisting of a carboxy group;
a hydroxy group;
a mercapto group;
a halogen atom;
a $C_{1-6}$ alkyloxy group;
a $C_{1-6}$ haloalkyloxy group;
a $C_{6-14}$ aryl group; and
a $C_{4-14}$ heteroaryl group;

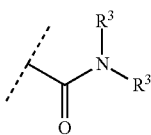

(3)

in the formula (3), two $R^3$ may be the same or different and each independently a 01-18 linear, branched or cyclic alkyl group which may be substituted, at a chemically acceptable optional position, by at least one substituent selected from the group consisting of
- a carboxy group;
- a hydroxy group;
- a mercapto group;
- a halogen atom;
- a $C_{1-6}$ alkyloxy group;
- a $C_{1-6}$ haloalkyloxy group;
- a $C_{6-14}$ aryl group; and
- a $C_{4-14}$ heteroaryl group;
- a $C_{6-14}$ aryl group,
- a $C_{4-14}$ heteroaryl group, or
- a hydrogen atom.

[4]. The aldehyde scavenger according to [3], wherein in the formula (1), $R^1$ is either a methyl group, an ethyl group, a propyl group, an isopropyl group, a butyl group, an isobutyl group, a sec-butyl group, a tert-butyl group, a benzyl group, a 2-pyridylmethyl group, a 3-pyridylmethyl, a 4-pyridylmethyl group, a carboxymethyl group, a 1-carboxyethyl group, a 2-carboxyethyl group, a 1-carboxypropyl group, a 2-carboxypropyl group, a 3-carboxypropyl group, an α-carboxy benzyl group, an α-carboxy-phenethyl group, a β-carboxy-phenethyl group, a 2-hydroxyethyl group, a 2-hydroxypropyl group, a 3-hydroxypropyl group, a 1-carboxy-2-hydroxyethyl group, an α-(methoxycarbonyl) benzyl group, an α-(methoxycarbonyl) phenethyl group, a β-(methoxycarbonyl) phenethyl group, a carbamoylmethyl group, an N-phenylcarbamoyl methyl group, an N-(2-carboxyphenyl) carbamoylmethyl group, an N-(3-carboxyphenyl) carbamoylmethyl group, an N-(4-carboxyphenyl) carbamoylmethyl group or an N-(2,6-dimethylphenyl) carbamoylmethyl group.

[5]. The aldehyde scavenger according to [1], wherein the O-substituted hydroxylamine is an O-substituted polyhydroxylamine.

[6]. The aldehyde scavenger according to [5], wherein the O-substituted polyhydroxylamine is at least one O-substituted polyhydroxylamine represented by the following formula (4):

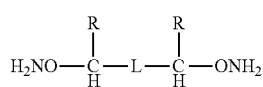

(4)

in the formula (4), L is a single bond; a $C_{1-8}$ linear, branched or cyclic alkylene group which may be substituted by at least one substituent selected from the group consisting of a $C_{1-6}$ alkyl group which may be substituted by a carboxy group, a hydroxy group, a mercapto group or an aminooxy group, a $C_{6-14}$ aryl group which may be substituted by a carboxy group, a hydroxy group or a mercapto group, and a $C_{4-14}$ heteroaryl group which may be substituted by a carboxy group, a hydroxy group or a mercapto group; a $C_{2-8}$ linear, branched or cyclic heteroalkylene group which may be substituted by at least one substituent selected from the group consisting of a $C_{1-6}$ alkyl group which may be substituted by a carboxy group, a hydroxy group, a mercapto group or an aminooxy group, a $C_{6-14}$ aryl group which may be substituted by a carboxy group, a hydroxy group or a mercapto group, and a $C_{4-14}$ heteroaryl group which may be substituted by a carboxy group, a hydroxy group or a mercapto group; a $C_{6-14}$ arylene group; or a $C_{4-14}$ heteroarylene group; and R is a hydrogen atom; a carboxy group; an aminooxy group; a $C_{1-6}$ alkyloxy group; a $C_{6-14}$ aryl group; a $C_{4-14}$ heteroaryl group; or a $C_{1-6}$ alkyl group which may be substituted by a carboxy group, a hydroxy group, a mercapto group or an aminooxy group; provided that two R may be the same or different.

[7] The aldehyde scavenger according to [6], wherein in the formula (4), L is either a single bond, a methylene group, a dimethylene group, a 1-methyl dimethylene group, a 1,1-dimethyl dimethylene group, a 1,2-dimethyl dimethylene group, a 1-ethyl-2-methyl dimethylene group, a trimethylene group, a 1-methyl trimethylene group, a 2-methyl trimethylene group, a tetramethylene group, a 1-methyl tetramethylene group, a 2-methyl tetramethylene group, a pentamethylene group, a hexamethylene group, a 1,3-cyclopentylene group, a 1,2-cyclohexylene group, a cyclohexylene-1,4-dimethylene group, an oxydimethylene group, an azadimethylene group, a thiadimethylene group, an oxydiethylene group, an azadiethylene group, a thiadiethylene group, a 2,5-dioxahexamethylene group, a 2,5-diazahexamethylene group, a 3,6-dioxa octamethylene group, a 3 6-diaza octamethylene group, a 1,2-phenylene group, a 1,4-phenylene group, a 1,2-phenylene dimethylene group, a pyridine-2,3-diyl group, a pyridine-2,6-diyl group, a pyridine-2,3-diyl-dimethylene group, or a pyridine-2,6-diyl-dimethylene group.

[8] The aldehyde scavenger according to [6] or [7], wherein in the formula (4), R is either a hydrogen atom, a methyl group, an ethyl group, a propyl group, an isopropyl group, a butyl group, an isobutyl group, a sec-butyl group, a tert-butyl group, a carboxy group, a hydroxymethyl group, a 2-hydroxyethyl group, a 3-hydroxypropyl group, a mercaptomethyl group, a 2-mercaptoethyl group, a 3-mercaptopropyl group, a carboxymethyl group, a 2-carboxyethyl group, a 3-carboxypropyl group, an aminooxy methyl group, or a 2-(aminooxy)ethyl group.

[9] A method for removing aldehydes, characterized by using the aldehyde scavenger as defined in any one of [1] to [8] against an aldehyde generation source.

Advantageous Effects of Invention

The aldehyde scavenger of the present invention, and the method of removing aldehydes by using it, will quickly and continuously capture aldehydes. As a result, it is possible to reduce aldehydes harmful to human bodies and to improve the human living environment.

DESCRIPTION OF EMBODIMENTS

Figure 1:
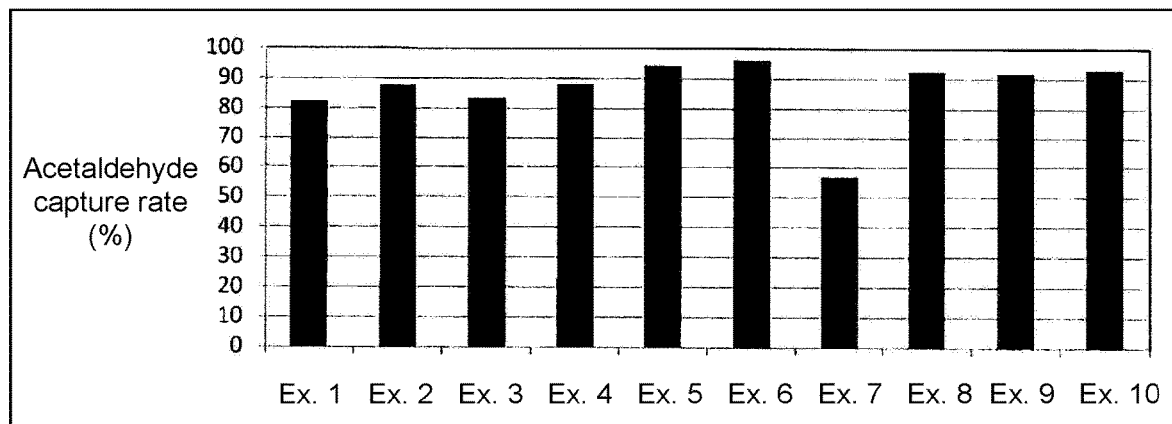
FIG. 1 is a diagram showing the acetaldehyde capture rates after 1 minute in Examples 1 to 26 and Comparative Examples 1 to 3.
Figure 1:
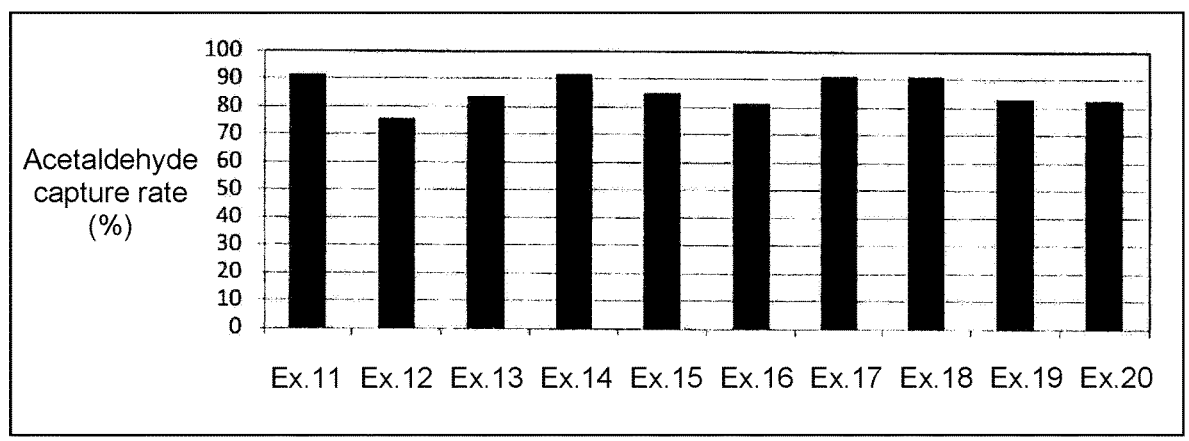
Figure 1:
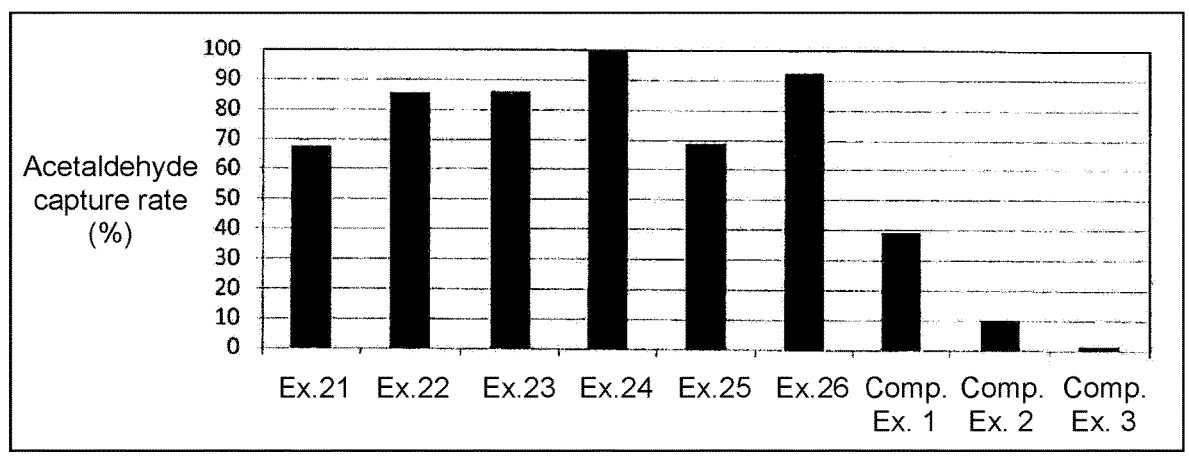

The aldehyde scavenger of the present invention is characterized by comprising at least one O-substituted hydroxylamine, or at least one chemically acceptable salt thereof.

(1)

In the formula (1) being the above-mentioned O-substituted mono hydroxylamine, $R^1$ is a 01-18 linear, branched or cyclic alkyl group which may be substituted, at an chemically acceptable optional position, by at least one substituent selected from the group consisting of
- a halogen atom;
- a $C_{1-6}$ alkyloxy group;
- a $C_{1-6}$ haloalkyl group;
- a $C_{1-6}$ haloalkyloxy group;
- a carboxy group;
- a hydroxy group;
- a mercapto group;
- a cyano group;
- a nitro group;
- a $C_{6-14}$ aryl group which may be substituted by a halogen atom, a $C_{1-6}$ alkyl group, a $C_{1-6}$ alkyloxy group, a $C_{1-6}$ haloalkyl group, a $C_{1-6}$ haloalkyloxy group, a carboxy group, a hydroxy group, a mercapto group, a cyano group or a nitro group;
- a $C_{4-14}$ heteroaryl group which may be substituted by a halogen atom, a $C_{1-6}$ alkyl group, a $C_{1-6}$ alkyloxy group, a $C_{1-6}$ haloalkyl group, a $C_{1-6}$ haloalkyloxy group, a carboxy group, a hydroxy group, a mercapto group, a cyano group or a nitro group;
- an alkoxycarbonyl group represented by the following formula (2); and
- a carbamoyl group represented by the following formula (3):

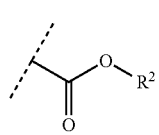
(2)

in the formula (2), $R^2$ is a 01-18 linear, branched or cyclic alkyl group which may be substituted, at a chemically acceptable optional position, by at least one substituent selected from the group consisting of
- a carboxy group;
- a hydroxy group;
- a mercapto group;
- a halogen atom;
- a $C_{1-6}$ alkyloxy group;
- a $C_{1-6}$ haloalkyloxy group;
- a $C_{6-14}$ aryl group; and
- a $C_{4-14}$ heteroaryl group;

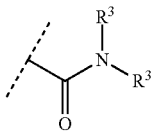
(3)

in the formula (3), two $R^3$ may be the same or different and each independently a 01-18 linear, branched or cyclic alkyl group which may be substituted, at a chemically acceptable optional position, by at least one substituent selected from the group consisting of
- a carboxy group;
- a hydroxy group;
- a mercapto group;
- a halogen atom;
- a $C_{1-6}$ alkyloxy group;
- a $C_{1-6}$ haloalkyloxy group;
- a $C_{6-14}$ aryl group; and
- a $C_{4-14}$ heteroaryl group;
- a $C_{6-14}$ aryl group,
- a $C_{4-14}$ heteroaryl group, or
- a hydrogen atom.

Here, the above $C_{1-18}$ linear, branched or cyclic alkyl group is not particularly limited, and may, for example, be a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group (cetyl group), a heptadecyl group, an octadecyl group (stearyl group), an oleyl group, an elaidyl group, an isopropyl group, an isobutyl group, a sec-butyl group, a tert-butyl group, a 3-methylbutyl group, a 2,2-dimethylpropyl group, a 1,1-dimethylpropyl group, a 2-ethylhexyl group, a cyclopropyl group, a cyclobutyl group, a cyclopentyl group, a cyclohexyl group, a cycloheptyl group, a cyclooctyl group, a cyclononyl group, a cyclodecyl group, etc.

The above alkyl group may be substituted by a halogen atom, a carboxyl group, a hydroxy group, a mercapto group, a cyano group, a nitro group, a $C_{1-6}$ alkyloxy group, a $C_{1-6}$ haloalkyl group, a $C_{1-6}$ haloalkyloxy group, a $C_{6-14}$ aryl group, a $C_{4-14}$ heteroaryl group, an alkoxycarbonyl group represented by the formula (2), and/or a carbamoyl group represented by the formula (3). As such substituents, substituents exemplified below may be mentioned.

As the above halogen atom, a fluorine atom, a chlorine atom, a bromine atom, etc. may be exemplified. The above $C_{1-6}$ alkyloxy group may be either linear, branched or cyclic, and a methoxy group, an ethoxy group, a propyloxy group, an isopropyloxy group, a butyloxy group, a pentyloxy group, a hexyloxy group, an isobutyloxy group, a sec-butyloxy group, a tert-butyloxy group, a 3-methyl butyloxy group, a 2,2-dimethylpropyloxy group, a 1,1-dimethylpropyloxy group, a 2-ethylhexyloxy group, a cyclopropyloxy group, a cyclobutyloxy group, a cyclopentyloxy group, a cyclohexyloxy group, etc. may be exemplified.

The above $C_{1-6}$ haloalkyl group may be either linear, branched or cyclic, and a difluoromethyl group, a trifluoromethyl group, a 2,2-difluoroethyl group, a 2,2,2-trifluoroethyl group, a 3-fluoropropyl group, a 1-(trifluoromethyl)-2,2,2-trifluoroethyl group, etc. may be exemplified.

The $C_{1-6}$ haloalkyloxy group may be either linear, branched or cyclic, and a difluoromethyloxy group, a trifluoromethyloxy group, a 2,2-difluoroethyloxy group, a 2,2, 2-trifluoroethyloxy group, a 3-fluoropropyloxy group, a 1-(trifluoromethyl)-2,2,2-trifluoroethyloxy group, etc. may be exemplified.

The above $C_{6-14}$ aryl group and $C_{4-14}$ heteroaryl group are not particularly limited, and, for example, a phenyl group, a naphthyl group, an anthryl group, a tolyl group, a xylyl group, a cumenyl group, a vinylphenyl group, a biphenylyl group, a phenanthryl group, a pyrrolyl group, a furyl group, a thienyl group, a pyridyl group, an indolyl group, a quinolyl group, an isoquinolyl group, etc. may be mentioned.

The aryl group and heteroaryl group may be substituted by a halogen atom, a $C_{1-6}$ alkyl group, a $C_{1-6}$ alkyloxy group, a $C_{1-6}$ haloalkyl group and/or a $C_{1-6}$ haloalkyloxy group, and as these substituents, substituents exemplified below may be mentioned.

The alkoxycarbonyl group represented by the above formula (2) is not particularly limited, and may, for example, be a methoxycarbonyl group, an ethoxycarbonyl group, a propyloxycarbonyl group, an isopropyloxycarbonyl group, a butyloxycarbonyl group, an isobutyloxycarbonyl group, a sec-butyloxycarbonyl group, a tert-butyloxycarbonyl group, a difluoromethyloxycarbonyl group, a trifluoromethyloxycarbonyl group, a phenyloxycarbonyl group, a naphthyloxycarbonyl group, a pyridyloxycarbonyl group, etc.

The carbamoyl group represented by the above formula (3) is not particularly limited, and may, for example, be a carbamoyl group, an N-methylcarbamoyl group, an N-ethylcarbamoyl group, an N-propylcarbamoyl group, an N-isopropylcarbamoyl group, N-butylcarbamoyl group, N-isobutylcarbamoyl group, N-(sec-butyl) carbamoyl group, an N-(tert-butyl) carbamoyl group, an N-difluoromethylcarbamoyl group, an N-trifluoromethylcarbamoyl group, an N-phenylcarbamoyl group, an N-naphthylcarbamoyl group, an N-pyridylcarbamoyl group, an N,N-dimethylcarbamoyl group, an N,N-diethylcarbamoyl group, an N,N-dipropylcarbamoyl group, an N,N-diisopropylcarbamoyl group, an N,N-dibutylcarbamoyl group, an N,N-diisobutylcarbamoyl group, an N,N-di(sec-butyl) carbamoyl group, an N,N-di(tert-butyl) carbamoyl group, an N,N-bis(difluoromethyl) carbamoyl group, an N,N-bis(trifluoromethyl) carbamoyl group, an N,N-diphenylcarbamoyl group, an N,N-dinaphthylcarbamoyl group, an N,N-dipyridylcarbamoyl group, etc.

The above $C_{1-6}$ alkyl group may be either linear, branched or cyclic, and a methyl group, an ethyl group, a propyl group, an isopropyl group, a butyl group, a pentyl group, a hexyl group, an isobutyl group, a sec-butyl group, a tert-butyl group, a 3-methylbutyl group, a 2,2-dimethylpropyl group, a 1,1-dimethylpropyl group, a 2-ethylhexyl group, a cyclopropyl group, a cyclobutyl group, a cyclopentyl group, a cyclohexyl group, etc. may be exemplified.

The above $C_{1-6}$ alkyloxy group may be either linear, branched or cyclic, and a methoxy group, an ethoxy group, a propyloxy group, an isopropyloxy group, a butyloxy group, a pentyloxy group, a hexyloxy group, an isobutyloxy group, a sec-butyloxy group, a tert-butyloxy group, a 3-methylbutyloxy group, a 2,2-dimethylpropyloxy group, a 1,1-dimethylpropyloxy group, a 2-ethylhexyloxy group, a cyclopropyloxy group, a cyclobutyloxy group, a cyclopentyloxy group, a cyclohexyloxy group, etc. may be exemplified.

The above $C_{1-6}$ haloalkyl group may be either linear, branched or cyclic, and a difluoromethyl group, a trifluoromethyl group, a 2,2-difluoroethyl group, a 2,2,2-trifluoroethyl group, a 3-fluoropropyl group, a 1-(trifluoromethyl)-2,2,2-trifluoroethyl group, etc. may be exemplified.

The above $C_{1-6}$ haloalkyloxy group may be either linear, branched or cyclic, and a difluoromethyloxy group, a trifluoromethyloxy group, a 2,2-difluoroethyloxy group, a 2,2,2-trifluoroethyloxy group, a 3-fluoropropyloxy group, a 1-(trifluoromethyl)-2,2,2-trifluoroethyloxy group, etc. may be exemplified.

Among them, preferred is an O-substituted mono hydroxylamine of the formula (1) wherein $R^1$ is a $C_{1-8}$ linear or branched alkyl group which may be substituted by a carboxy group, a hydroxy group, a mercapto group, a $C_{6-14}$ aryl group or a $C_{4-14}$ heteroaryl group, and particularly preferred is an O-substituted mono hydroxylamine wherein $R^1$ is either a methyl group, an ethyl group, a propyl group, an isopropyl group, a butyl group, an isobutyl group, a sec-butyl group, a tert-butyl group, a benzyl group, a 2-pyridylmethyl group, a 3-pyridylmethyl group, a 4-pyridylmethyl group, a carboxymethyl group, a 1-carboxyethyl group, a 1-carboxypropyl group, a 3-carboxypropyl group, an α-carboxy benzyl group, an α-carboxy-phenethyl group, a β-carboxy-phenethyl group, a 2-hydroxyethyl group, a 2-hydroxypropyl group, a 3-hydroxypropyl group, a 1-carboxy-2-hydroxyethyl group, an α-(methoxycarbonyl) benzyl group, an α-(methoxycarbonyl) phenethyl group, a carbamoylmethyl group, a β-(methoxycarbonyl) phenethyl group, a carbamoylmethyl group, an N-phenylcarbamoyl methyl group, an N-(2-carboxyphenyl) carbamoylmethyl group, an N-(3-carboxyphenyl) carbamoylmethyl group, an N-(4-carboxyphenyl) carbamoylmethyl group or an N-(2,6-dimethylphenyl) carbamoylmethyl group.

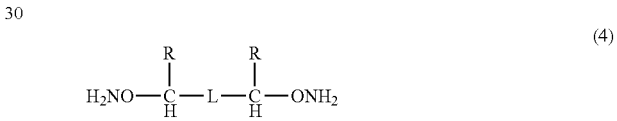

(4)

In the formula (4) being the above-mentioned O-substituted polyhydroxylamine, L is a single bond; a $C_{1-8}$ linear, branched or cyclic alkylene group which may be substituted by at least one substituent selected from the group consisting of a $C_{1-6}$ alkyl group which may be substituted by a carboxy group, a hydroxy group, a mercapto group or an aminooxy group, a $C_{6-14}$ aryl group which may be substituted by a carboxy group, a hydroxy group or a mercapto group, and a $C_{4-14}$ heteroaryl group which may be substituted by a carboxy group, a hydroxy group or a mercapto group; a $C_{2-8}$ linear, branched or cyclic heteroalkylene group which may be substituted by at least one substituent selected from the group consisting of a $C_{1-6}$ alkyl group which may be substituted by a carboxy group, a hydroxy group, a mercapto group or an aminooxy group, a $C_{6-14}$ aryl group which may be substituted by a carboxy group, a hydroxy group or a mercapto group, and a $C_{4-14}$ heteroaryl group which may be substituted by a carboxy group, a hydroxy group or a mercapto group; a $C_{6-14}$ arylene group; or a $C_{4-14}$ heteroarylene group.

R is a hydrogen atom; a carboxy group; an aminooxy group; a $C_{1-6}$ alkyloxy group; a $C_{6-14}$ aryl group; a $C_{4-14}$ heteroaryl group; or a $C_{1-6}$ alkyl group which may be substituted by a carboxy group, a hydroxy group, a mercapto group or an aminooxy group; provided that two R may be the same or different.

The $C_{1-8}$ alkylene group and $C_{2-8}$ heteroalkylene group represented by L are not particularly limited, and the alkylene group and heteroalkylene group may be either linear, branched or cyclic. For example, a methylene group, a dimethylene group, a 1-methyl dimethylene group, a 1,1-dimethyl dimethylene group, a 1,2-dimethyl dimethylene group, a 1-ethyl-2-methyl dimethylene group, a trimethylene group, a 1-methyltrimethylene group, a 2-methyltrimethylene group, a 2-ethyltrimethylene group, a 2-propyltrimethylene group, a tetramethylene group, a 1-methyltetramethylene group, a 2-methyltetramethylene group, a pentamethylene group, a hexamethylene group, a heptamethylene group, an octamethylene group, a cyclopropylene group, a 1,2-cyclobutylene group, a 1,3 cyclobutylene group, a 1,2-cyclopentylene group, a 1,3-cyclopentylene group, a 1,2-cyclohexylene group, a 1,3-cyclohexylene group, a 1,4-cyclohexylene group, a cyclohexylene-1,3-dimethylene group, a cyclohexylene-1,4-dimethylene group, a 1,2-cycloheptylene, a 1,2-cyclooctylene group, an oxydimethylene group, an azadimethylene group, a thiadimethylene group, an oxydiethylene group, an azadiethylene group, a thiadiethylene group, a 2,5-dioxahexamethylene group, a 2,5-diazahexamethylene group, a 3,6-dioxaoctamethylene group, a 3,6-diazaoctamethylene group, 1,2-, 1,3- or 1,4-phenylene dimethylene group, a 1,2- or 1,4-phenylene diethylene group, a pyridine-2,3-diyl-dimethylene group, a pyridine-2,4-diyl-dimethylene group, a pyridine-2,5-diyl-dimethylene group, a pyridine-2,6-diyl-dimethylene group, a pyridine-3,5-diyl-dimethylene group, etc. may be mentioned.

The above alkylene group and heteroalkylene group may be substituted by a $C_{1-6}$ alkyl group which may be substituted by a carboxy group, a hydroxy group, a mercapto group or an aminooxy group; a $C_{6-14}$ aryl group which may be substituted by a carboxy group, a hydroxy group or a mercapto group; and/or a $C_{4-14}$ heteroaryl group which may be substituted by a carboxy group, a hydroxy group or mercapto group.

As the alkyl group in the $C_{1-6}$ alkyl group which may be substituted by a carboxy group, a hydroxy group, a mercapto group or an amino-oxy group, a methyl group, an ethyl group, a propyl group, an isopropyl group, a tert-butyl group, a hexyl group, etc. may be exemplified.

As the aryl group in the $C_{6-14}$ aryl group which may be substituted by a carboxyl group, a hydroxy group or a mercapto group, a phenyl group, a naphthyl group, an anthryl group, a biphenyl group, a phenanthryl group, etc. may be exemplified.

As the ring constituting the heteroaryl group in the above $C_{4-14}$ heteroaryl group which may be substituted by a carboxy group, a hydroxy group or a mercapto group, a pyrrole ring, a furan ring, a thiophene ring, a pyrazole ring, an imidazole ring, a pyridine ring, a pyrazine ring, an indole ring, a quinoline ring, an isoquinoline ring, etc. may be mentioned.

The $C_{6-14}$ arylene group represented by L may, for example, be a 1,2-, 1,3- or 1,4-phenylene group, a 1,2-, 1,4-, 1,5-, 1,8, 2,3- or 2,6-naphthylene group, a 1,2-, 1,4-, 1,9-, 1,10-, 2,3- or 2,7-anthrylene group, a biphenylene group, a phenanthrylene group, etc., and the aryl group of the arylene group may be substituted by a $C_{1-6}$ alkyl group such as a methyl group, an ethyl group, a propyl group, an isopropyl group, a tert-butyl group or a hexyl group, or a $C_{2-6}$ alkenyl group such as a vinyl group, a propenyl group, a butenyl group or a hexenyl group.

Specific examples of the ring constituting the $C_{4-14}$ heteroarylene group represented by L, include a pyrrole ring, a furan ring, a thiophene ring, a pyrazole ring, an imidazole ring, a pyridine ring, a pyrazine ring, an indole ring, a quinoline ring, an isoquinoline ring, etc., and the heteroaryl group of the heteroarylene group may be substituted by a $C_{1-6}$ alkyl group such as a methyl group, an ethyl group, a propyl group, an isopropyl group, a tert-butyl group or a hexyl group, or a $C_{2-6}$ alkenyl group such as a vinyl group, a propenyl group, a butenyl group or a hexenyl group.

Among the above exemplified substituents L, particularly preferred is an O-substituted polyhydroxylamine of the formula (4) wherein L is either a single bond, a methylene group, a dimethylene group, a 1-methyl dimethylene group, a 1,1-dimethyl dimethylene group, a 1,2-dimethyl dimethylene group, a 1-ethyl-2-methyl dimethylene group, a trimethylene group, a 1-methyltrimethylene group, a 2-methyltrimethylene group, a tetramethylene group, a 1-methyl tetramethylene group, a 2-methyltetramethylene group, a pentamethylene group, a hexamethylene group, a 1,3-cyclopentylene group, a 1,2-cyclohexylene group, a cyclohexylene-1,4-dimethylene group, an oxydimethylene group, an azadimethylene group, a thiadimethylene group, an oxydiethylene group, an azadiethylene group, a thiadiethylene group, a 2,5-dioxa hexamethylene group, a 2,5-diaza hexamethylene group, a 3,6-dioxa octamethylene group, a 3,6-diaza octamethylene group, a 1,2-phenylene group, a 1,4-phenylene group, a 1,2-phenylene dimethylene group, a pyridine-2,3-diyl group, a pyridine-2,6-diyl group, a pyridine-2,3-diyl-dimethylene group, or a pyridine-2,6-diyl-dimethylene group.

As the $C_{1-6}$ alkyloxy group represented by R, a methoxy group, an ethoxy group, a propyloxy group, an isopropyloxy group, a butyloxy group, an isobutyloxy group, a sec-butyloxy group, a tert-butyloxy group, a pentyloxy group, a 2-methyl butyloxy group, a pentan-2-yloxy group, a tert-pentyloxy group, a neopentyloxy group, a hexyloxy group, a 2-methylpentyloxy group, a 3-methylpentyloxy group, a 4-methylpentyloxy group, a hexan-2-yloxy group, a 2-methylpentan-2-yloxy group, a 2,2-dimethylbutyloxy group, a 2,3-dimethylbutyloxy group, a 3,3-dimethylbutyloxy group, a 3-methylpentan-2-yloxy group, a 4-methylpentan-2-yloxy group, a 2,3-dimethylbutan-2-yloxy group, a 3,3-dimethylbutan-2-yloxy group, etc. may be mentioned.

As the $C_{6-14}$ aryl group represented by R, a phenyl group, a naphthyl group, an anthryl group, a biphenylyl group, a phenanthryl group, etc. may be mentioned, and the aryl group may be substituted by a $C_{1-6}$ alkyl group such as a methyl group, an ethyl group, a propyl group, an isopropyl group, a tert-butyl group or a hexyl group, a $C_{1-6}$ alkyloxy group such as a methoxy group, an ethoxy group, a propyloxy group, an isopropyloxy group, a tert-butyloxy group or a hexyloxy group, or a $C_{2-6}$ alkenyl group, such as a vinyl group, a propenyl group, a butenyl group or a hexenyl group.

As the ring constituting the $C_{4-14}$ heteroaryl group represented by R, a pyrrole ring, a furan ring, a thiophene ring, a pyrazole ring, an imidazole ring, a pyridine ring, a pyrazine ring, an indole ring, a quinoline ring, an isoquinoline ring, etc. may be mentioned, and the heteroaryl group may be substituted by a $C_{1-6}$ alkyl group such as a methyl group, an ethyl group, a propyl group, an isopropyl group, a tert-butyl group or a hexyl group, a $C_{1-6}$ alkyloxy group such as a methoxy group, an ethoxy group, a propyloxy group, an isopropyloxy group, a tert-butyloxy group or a hexyloxy group, or a $C_{2-6}$ alkenyl group such as a vinyl group, a propenyl group, a butenyl group, a hexenyl group.

The $C_{1-6}$ alkyl group which may be substituted by a carboxy group, a hydroxy group, a mercapto group or an aminooxy group, represented by R, includes an alkyl group such as a methyl group, an ethyl group, a propyl group, an isopropyl group, a butyl group, an isobutyl group, a sec-butyl group, a tert-butyl group, a pentyl group, a 2-methylbutyl group, a pentan-2-yl group, a tert-pentyl group, a neopentyl group, a hexyl group, a 2-methylpentyl group, a 3-methylpentyl group, a 4-methylpentyl group, a hexan-2-yl group, a 2-methylpentan-2-yl group, a 2,2-dimethylbutyl group, a 2,3-dimethylbutyl group, a 3,3-dimethylbutyl group, a 3-methylpentan-2-yl group, a 4-methylpentan-2-yl group, a 2,3-dimethylbutan-2-yl group, a 3,3-dimethylbutan-2-yl group, etc.; an alkyl group substituted by a carboxy group such as a carboxymethyl group, a 1-carboxyethyl group, a 2-carboxyethyl group, a 1-carboxypropyl group, a 2-carboxypropyl group, a 3-carboxypropyl group, an α-carboxy isopropyl group, a β-carboxy isopropyl group, a 1-carboxybutyl group, a 2-carboxybutyl group, a 3-carboxybutyl group, a 4-carboxybutyl group, an α-carboxyisobutyl group, a 1-carboxy-1-methylpropyl group, a β-carboxy isobutyl group, a 2-carboxy-1,1-dimethylethyl group, a γ-carboxy isobutyl group, a 3-carboxy-1-methylpropyl group, a 1-carboxypentyl group, a 1-carboxy-1-methylbutyl group, a 1-carboxy-2-methylbutyl group, a 1-carboxy-3-methylbutyl group, a 1-carboxy-1,2-dimethylpropyl group, a 1-carboxy-2,2-dimethylpropyl group, a 2-carboxypentyl group, a 2-carboxy-1-methylbutyl group, a 2-carboxy-2-methylbutyl group, a 2-carboxy-3-methylbutyl group, a 2-carboxy-1,1-dimethylpropyl group, a 2-carboxy-1,2-dimethylpropyl group, a 3-carboxypentyl group, a 3-carboxy-1,1-dimethylpropyl group, a 3-carboxy-1,2-dimethylpropyl group, a 3-carboxy-1,3-dimethylpropyl group, a 3-carboxy-2,2-dimethylpropyl group, a 3-carboxy-2,3-dimethylpropyl group, a 3-carboxy-3,3-dimethylpropyl group, a 4-carboxypentyl group, a 4-carboxy-1-methylbutyl group, a 4-carboxy-2-methylbutyl group, a 4-carboxy-3-methylbutyl group, a 5-carboxypentyl group, etc.; an alkyl group substituted by a hydroxyl group such as a hydroxymethyl group, a 1-hydroxyethyl group, a 2-hydroxyethyl group, a 1-hydroxypropyl group, a 2-hydroxypropyl group, a 3-hydroxypropyl group, an α-hydroxy isopropyl group, a β-hydroxy isopropyl group, a 1-hydroxybutyl group, a 2-hydroxybutyl group, a 3-hydroxybutyl group, a 4-hydroxybutyl group, an α-hydroxy isobutyl group, a 1-hydroxy-1-methylpropyl group, a β-hydroxy isobutyl group, a 2-hydroxy-1,1-dimethylethyl group, a γ-hydroxy isobutyl group, a 3-hydroxy-1-methylpropyl group, a 1-hydroxypentyl group, a 1-hydroxy-1-methylbutyl group, a 1-hydroxy-2-methylbutyl group, a 1-hydroxy-3-methylbutyl group, a 1-hydroxy-1,2-dimethylpropyl group, a 1-hydroxy-2,2-dimethylpropyl group, a 2-hydroxypentyl group, a 2-hydroxy-1-methylbutyl group, a 2-hydroxy-2-methylbutyl group, a 2-hydroxy-3-methylbutyl group, a 2-hydroxy-1,1-dimethylpropyl group, a 2-hydroxy-1,2-dimethylpropyl group, a 3-hydroxypentyl group, a 3-hydroxy-1,1-dimethylpropyl group, a 3-hydroxy-1,2-dimethylpropyl group, a 3-hydroxy-1,3-dimethylpropyl group, a 3-hydroxy 2,2-dimethylpropyl group, a 3-hydroxy-2,3-dimethylpropyl group, a 3-hydroxy-3,3-dimethylpropyl group, a 4-hydroxypentyl group, a 4-hydroxy-1-methylbutyl group, a 4-hydroxy-2-methylbutyl group, a 4-hydroxy-3-methylbutyl group, a 5-hydroxypentyl group, etc.; an alkyl group substituted by a mercapto group, such as a mercaptomethyl group, a 1-mercaptoethyl group, a 2-mercaptoethyl group, a 1-mercaptopropyl group, a 2-mercaptopropyl group, a 3-mercaptopropyl group, an α-mercaptoisopropyl group, a β-mercaptoisopropyl group, a 1-mercaptobutyl group, a 2-mercaptobutyl group, a 3-mercaptobutyl group, a 4-mercaptobutyl group, an α-mercapto isobutyl group, a 1-mercapto-1-methylpropyl group, a β-mercapto isobutyl group, a 2-mercapto-1,1-dimethylethyl group, a γ-mercapto isobutyl group, a 3-mercapto-1-methylpropyl group, a 1-mercaptopentyl group, a 1-mercapto-1-methylbutyl group, a 1-mercapto-2-methylbutyl group, a 1-mercapto-3-methylbutyl group, a 1-mercapto-1,2-dimethylpropyl group, a 1-mercapto-2,2-dimethylpropyl group, a 2-mercapto pentyl group, a 2-mercapto-1-methylbutyl group, a 2-mercapto-2-methylbutyl group, a 2-mercapto-3-methylbutyl group, a 2-mercapto-1,1-dimethylpropyl group, a 2-mercapto-1,2-dimethylpropyl group, a 3-mercaptopentyl group, a 3-mercapto-1,1-dimethylpropyl group, a 3-mercapto-1,2-dimethylpropyl group, a 3-mercapto-1,3-dimethylpropyl group, a 3-mercapto-2,2-dimethylpropyl group, a 3-mercapto-2,3-dimethylpropyl group, a 3-mercapto-3,3-dimethylpropyl group, a 4-mercaptopentyl group, a 4-mercapto-1-methylbutyl group, a 4-mercapto-2-m ethylbutyl group, a 4-mercapto-3-m ethylbutyl group, a 5-mercaptopentyl group, etc.; and an alkyl group substituted by an aminooxy group, such as an (aminooxy) methyl group, a 1-(aminooxy) ethyl group, a 2-(aminooxy) ethyl group, a 1-(aminooxy) propyl group, a 2-(aminooxy) propyl group, a 3-(aminooxy) propyl group, an α-(aminooxy) isopropyl group, a β-(aminooxy) isopropyl group, a 1-(aminooxy) butyl group, a 2-(aminooxy) butyl group, a 3-(aminooxy) butyl group, a 4-(aminooxy) butyl group, an α-(aminooxy) isobutyl group, a 1-(aminooxy)-1-methylpropyl group, a β-(aminooxy) isobutyl group, a 2-(aminooxy)-1,1-dimethylethyl group, a γ-(aminooxy) isobutyl group, a 3-(aminooxy)-1-methylpropyl group, a 1-(aminooxy) pentyl group, a 1-(aminooxy)-1-methylbutyl group, a 1-(aminooxy)-2-methylbutyl group, a 1-(aminooxy)-3-methylbutyl group, a 1-(aminooxy)-1,2-dimethylpropyl group, a 1-(aminooxy)-2,2-dimethylpropyl group, a 2-(aminooxy) pentyl group, a 2-(aminooxy)-1-methylbutyl group, a 2-(aminooxy)-2-methylbutyl group, a 2-(aminooxy)-3-methylbutyl group, a 2-(aminooxy)-1,1-dimethylpropyl group, a 2-(aminooxy)-1,2-dimethylpropyl group, a 3-(aminooxy) pentyl group, a 3-(aminooxy)-1,1-dimethylpropyl group, a 3-(aminooxy)-1,2-dimethylpropyl group, a 3-(aminooxy)-1,3-dimethylpropyl group, a 3-(aminooxy)-2,2-dimethylpropyl group, a 3-(aminooxy)-2,3-dimethylpropyl group, a 3-(aminooxy)-3,3-dimethylpropyl group, a 4-(aminooxy) pentyl group, a 4-(aminooxy)-1-methylbutyl group, a 4-(aminooxy)-2-methylbutyl group, a 4-(aminooxy)-3-methylbutyl group, a 5-(aminooxy) pentyl group, etc.

Among the above exemplification, preferred is an O-substituted polyhydroxylamine of the formula (4) wherein R is either a hydrogen atom, a methyl group, an ethyl group, a propyl group, an isopropyl group, a butyl group, an isobutyl group, a sec-butyl group, a tert-butyl group, a carboxy group, a hydroxymethyl group, a 2-hydroxyethyl group, a 3-hydroxypropyl group, a mercaptomethyl group, a 2-mercaptoethyl group, a 3-mercaptopropyl group, a carboxymethyl group, a 2-carboxyethyl group, a 3-carboxypropyl group, an aminooxy methyl group or a 2-(aminooxy) ethyl group, and especially preferred is a case when R is a hydrogen atom.

The above O-substituted hydroxylamine may be such that part or all thereof is a chemically acceptable salt with an inorganic or organic acid. The type of the salt is not particularly limited, but may, for example, be an inorganic acid salt such as a hydrochloride, a hydrobromide, a perchlorate, a silicate, a tetrafluoroborate, a hexafluorophosphate, a sulfate, a nitrate, a phosphate, etc., or an organic acid salt such as an acetate, a citrate, a fumarate, a maleate, a trifluoromethanesulfonate, a trifluoroacetate, a benzoate, a p-toluenesulfonic acid salt, etc., and from the viewpoint of inexpensiveness, an inorganic acid salt is preferred, and a hydrochloride is more preferred.

Further, in a case where the O-substituted hydroxylamine contains an amino group, part or all of the amino group may be a chemically acceptable salt with the inorganic or organic acid.

On the other hand, in a case where the O-substituted hydroxylamine contains a carboxy group, the carboxy group may form an intramolecular salt with a hydroxyl amino group or an amino group in the molecule. Also, part or all of the carboxy group may be in the form of a carboxylic acid salt. The type of carboxylic acid salt is not particularly limited, and may, for example, be an alkali metal salt such as a lithium salt, a sodium salt, a potassium salt, a cesium salt, etc., or an ammonium salt.

The aldehyde scavenger of the present invention may be used in an optional form depending upon the object or application. For example, an O-substituted hydroxylamine or its chemically acceptable salt (hereinafter referred to as "the O-substituted hydroxylamine") may be dissolved in an optional solvent and used as a liquid aldehyde scavenger; the O-substituted hydroxylamine or the above liquid aldehyde scavenger may be supported on an optional carrier and used as a solid aldehyde scavenger; or may be used as kneaded in e.g. rubber, etc. Further, by applying these scavengers to the material to be an aldehyde generating source such as a plywood or an automobile ceiling material, it is possible to suppress release of aldehydes from the material into the environment.

The dissolution amount of the O-substituted hydroxylamine in a solvent at the time of preparing the liquid aldehyde scavenger of the present invention, is suitably adjustable depending on the purpose and is not particularly limited, but in the liquid aldehyde scavenger of the present invention, the content of the aldehyde scavenger is preferably within a range of from 1 to 50 wt %, more preferably within a range of from 5 to 30 wt %.

As the carrier to support the O-substituted hydroxylamine at the time of preparing the solid aldehyde scavenger of the present invention, one insoluble in water may be used without any particular limitation. For example, as a polymeric carrier, a styrene type polymer such as polystyrene, crosslinked polystyrene, etc., a polyolefin such as polyethylene, polypropylene, etc., a poly(halogenated)olefin such as polyvinyl chloride, polytetrafluoroethylene, etc., a nitrile polymer such as polyacrylonitrile, etc., a (meth)acrylic polymer such as polymethyl methacrylate, polyethyl acrylate, etc., or a high molecular weight polysaccharide such as cellulose, agarose, dextran, etc., may be mentioned, and as an inorganic carrier, activated carbon, silica gel, diatomaceous earth, hydroxyapatite, alumina, titanium oxide, magnesia, polysiloxane, etc. may be mentioned.

Here, the cross-linked polystyrene is one composed mainly of a cross-linked copolymer of a monovinyl aromatic compound such as styrene, vinyl toluene, vinyl xylene, vinyl naphthalene, etc. and a polyvinyl aromatic compound such as divinyl benzene, divinyl toluene, divinyl xylene, divinyl naphthalene, trivinyl benzene, bis vinyl diphenyl, bis vinyl phenyl ethane, etc., and to such a crosslinked copolymer, a methacrylic acid ester such as glycerol methacrylate, ethylene glycol dimethacrylate, etc. may be copolymerized.

The shape of the carrier to be used in the preparation of the solid aldehyde scavenger of the present invention is not particularly limited, and a shape to be commonly used as permeable substrate, for example, spherical (e.g. spherical particles, etc.), particulate, fibrous, granular, monolith column, hollow yarn, film-like (e.g. a flat membrane, etc.), etc. may be employed, and, among these, a spherical, membrane-like, particulate, granular or fibrous one is preferred. A spherical, particulate or granular carrier is particularly preferably used, since the volume to be used can be freely set at the time of using it in a column method or a batch method.

With respect to the particle size of the spherical, particulate or granular carrier, usually, it is possible to use one having an average particle size within a range of from 1 μm to 10 mm, but a range of from 2 μm to 1 mm is preferred. Here, the average particle size means the 50% volume average particle diameter (D50).

The carrier to be used in the preparation of the solid aldehyde scavenger of the present invention may be a porous, or non-porous. As the average pore diameter of the porous carrier, one of from 1 nm to 1 μm may usually be used, but from the viewpoint of the aldehyde capturing speed, a range of 1 nm to 300 nm is preferred.

The method for preparing the solid aldehyde scavenger of the present invention is not particularly limited, but, for example, a method of letting the liquid aldehyde scavenger or the O-substituted hydroxylamine of the present invention be physically adsorbed and fixed on the carrier, may be mentioned.

The method of letting the O-substituted hydroxylamine be physically adsorbed and fixed, is not particularly limited, but, for example, a method of letting the O-substituted hydroxylamine be dissolved in a solvent such as water, then adding the above-mentioned carrier to let the O-substituted hydroxylamine be impregnated to the carrier, and further distilling off the solvent, may be mentioned.

The supported amount of the O-substituted hydroxylamine on the carrier is optionally adjustable depending upon the purpose, and is not particularly limited, but the O-substituted hydroxylamine is preferably with in a range of from 1 to 50 wt %, more preferably within a range of from 5 to 30 wt %.

The aldehyde scavenger of the present invention, and the method of capturing aldehydes by using it, are applicable to aldehydes having aldehyde groups, inter alia, to $C_{1-8}$, in particular, $C_{1-4}$ aldehydes, inter alia, to acetaldehyde and formaldehyde.

EXAMPLES

Hereinafter, the present invention will be described in detail, but the present invention should not to be construed as being limited to these Examples.

Here, in the following Examples, the aldehyde capture rate was calculated from the following formula.

Aldehyde capture rate (%)=[(acetaldehyde initial concentration−residual acetaldehyde concentration)/acetaldehyde initial concentration]×100

Examples 1 to 26 (Aldehyde Capture Test in an Aqueous Solution)

An O-substituted mono hydroxylamine (0.23 mmol) was dissolved in water (5 mL) to prepare an aldehyde scavenger. Thereto, an aqueous solution 5 mL containing acetaldehyde (0.23 mmol) and diethylene glycol diethyl ether (0.2 wt %) as the internal standard substance, was mixed. After 1 minute, after 5 minutes, after 10 minutes and after 30 minutes, a portion (0.2 mL) of the reaction liquid was withdrawn, and thereto, sodium borohydride 1 mg was added, to reduce remaining acetaldehyde to ethanol. This solution was analyzed by gas chromatograph (GC-2014, manufactured by Shimadzu Corporation), and the residual acetaldehyde concentration was calculated from the area ratio of ethanol and diethylene glycol diethyl ether.

Comparative Examples 1 to 3

The operation was carried out in the same manner as in Examples 1 to 26 except that in place of the O-substituted mono hydroxylamine, Chem catch H-6000HS (hydrazide type, manufactured by Otsuka Chemical Co., Ltd.), piperazine (amine type), or glycine (amino acid-type), as a conventional product, was used.

The results (capture rates from after 1 minute to after 30 minutes) in Examples 1 to 26 and Comparative Examples 1 to 3, are shown in Table 1, Table 2 and FIG. 1 (capture rate after 1 minute).

TABLE 1

| | Ex. 1 | Ex. 2 | Ex. 3 |
|---|---|---|---|
| Compound | Me—ONH$_2$ •HCl | (CH$_3$)$_2$CH—ONH$_2$ •HCl | (CH$_3$)$_3$C—ONH$_2$ •HCl |
| Capture rate (%) after 1 min | 82.3 | 87.5 | 83.2 |
| Capture rate (%) after 5 min | 94.0 | 95.3 | 95.4 |
| Capture rate (%) after 10 min | 96.7 | 97.9 | 97.9 |
| Capture rate (%) after 30 min | 98.2 | 99.0 | 99.1 |

| | Ex. 4 | Ex. 5 | Ex. 6 |
|---|---|---|---|
| Compound | PhCH$_2$—ONH$_2$ •HCl | HOOC-CH$_2$-ONH$_2$ •0.5 HCl | HOOC-CH$_2$-ONH$_2$ |
| Capture rate (%) after 1 min | 88.3 | 94.2 | 96.2 |
| Capture rate (%) after 5 min | 97.1 | 97.5 | 99.7 |
| Capture rate (%) after 10 min | 98.7 | >99.9 | >99.9 |
| Capture rate (%) after 30 min | 99.3 | >99.9 | >99.9 |

| | Ex. 7 | Ex. 8 | Ex. 9 |
|---|---|---|---|
| Compound | NaOOC-CH$_2$-ONH$_2$ | HOOC-CH$_2$-ONH$_2$ •0.5 H$_2$SO$_4$ | HOOC-CH$_2$-ONH$_2$ •0.5 tosyl acid |
| Capture rate (%) after 1 min | 57.0 | 92.1 | 91.9 |
| Capture rate (%) after 5 min | 94.3 | 97.8 | 97.8 |
| Capture rate (%) after 10 min | 95.8 | 99.6 | 99.0 |
| Capture rate (%) after 30 min | 95.9 | 99.8 | 99.1 |

| | Ex. 10 | Ex. 11 | Ex. 12 |
|---|---|---|---|
| Compound | HOOC-CH(CH$_3$)-ONH$_2$ •0.5 HCl | HOOC-CH(C$_2$H$_5$)-ONH$_2$ •0.5 HCl | HOOC-(CH$_2$)$_3$-ONH$_2$ •0.5 HCl |
| Capture rate (%) after 1 min | 92.8 | 91.8 | 75.9 |
| Capture rate (%) after 5 min | 96.1 | 95.5 | 93.3 |
| Capture rate (%) after 10 min | 98.4 | 98.0 | 93.9 |
| Capture rate (%) after 30 min | >99.9 | >99.9 | 94.5 |

TABLE 1-continued

| Compound | Ex. 13 (HO-CH(iPr)-C(=O)-ONH₂ · 0.5 HCl) | Ex. 14 (HO-CH(iBu)-C(=O)-ONH₂ · 0.5 HCl) | Ex. 15 (HO-CH(CH₂Ph)-C(=O)-ONH₂ · 0.5 HCl) |
|---|---|---|---|
| Capture rate (%) after 1 min | 83.5 | 91.9 | 84.9 |
| Capture rate (%) after 5 min | 94.6 | 98.6 | 87.7 |
| Capture rate (%) after 10 min | 95.1 | 99.5 | 89.9 |
| Capture rate (%) after 30 min | 95.4 | >99.9 | 91.7 |

| Compound | Ex. 16 (HO-CH(CH₂OH)-C(=O)-ONH₂ · 0.5 HCl) | Ex. 17 (HO-CH(Ph)-C(=O)-ONH₂ · 0.5 HCl) | Ex. 18 (2-HOOC-C₆H₄-NH-C(=O)-CH₂-ONH₂ · 0.5 HCl) |
|---|---|---|---|
| Capture rate (%) after 1 min | 81.6 | 90.8 | 90.8 |
| Capture rate (%) after 5 min | 83.6 | 99.2 | 94.3 |
| Capture rate (%) after 10 min | 84.1 | >99.9 | 94.5 |
| Capture rate (%) after 30 min | 84.8 | >99.9 | 94.8 |

TABLE 2

| Compound | Ex. 19 (3-HOOC-C₆H₄-NH-C(=O)-CH₂-ONH₂ · 0.5 HCl) | Ex. 20 (4-HOOC-C₆H₄-NH-C(=O)-CH₂-ONH₂ · 0.5 HCl) |
|---|---|---|
| Capture rate (%) after 1 min | 83.2 | 82.3 |
| Capture rate (%) after 5 min | 86.2 | 85.6 |
| Capture rate (%) after 10 min | 86.9 | 87.5 |
| Capture rate (%) after 30 min | 87.7 | 88.9 |

| Compound | Ex. 21 (MeO-C(=O)-CH(CH₂OH)-ONH₂) | Ex. 22 (H₂N-C(=O)-CH₂-ONH₂ · HCl) |
|---|---|---|
| Capture rate (%) after 1 min | 67.2 | 85.4 |
| Capture rate (%) after 5 min | 70.0 | 86.0 |
| Capture rate (%) after 10 min | 71.0 | 86.2 |
| Capture rate (%) after 30 min | 71.2 | 86.5 |

TABLE 2-continued

| | Ex. 23 | Ex. 24 |
|---|---|---|
| Compound | 2,6-dimethylphenyl-NH-C(O)-CH2-ONH2 · HCl | pyridin-3-yl-CH2-ONH2 · HCl |
| Capture rate (%) after 1 min | 85.7 | 99.5 |
| Capture rate (%) after 5 min | 86.4 | 99.6 |
| Capture rate (%) after 10 min | 87.1 | 99.6 |
| Capture rate (%) after 30 min | 87.6 | 99.7 |

| | Ex. 25 | Ex. 26 |
|---|---|---|
| Compound | HO-(CH2)n-ONH2 | HOOC-CH(NH2)-CH2-ONH2 · 2 HCl |
| Capture rate (%) after 1 min | 68.8 | 92.1 |
| Capture rate (%) after 5 min | 83.4 | 97.7 |
| Capture rate (%) after 10 min | 92.0 | 98.0 |
| Capture rate (%) after 30 min | 96.1 | 98.2 |

| | Comp. Ex. 1 | Comp. Ex. 2 | Comp. Ex. 3 |
|---|---|---|---|
| Compound | Chem catch H-6000HS | piperazine | HO-C(O)-CH2-NH2 |
| Capture rate (%) after 1 min | 39.4 | 9.9 | 1.2 |
| Capture rate (%) after 5 min | 71.2 | 15.4 | 1.5 |
| Capture rate (%) after 10 min | 82.6 | 20.6 | 1.7 |
| Capture rate (%) after 30 min | 91.3 | 25.2 | 1.8 |

As evident from Table 1, Table 2 and FIG. 1, the aldehyde scavengers of the present invention showed a high aldehyde capture performance in aqueous solutions especially at an initial stage as compared to the conventional aldehyde scavengers.

Example 27

As a result of the operation carried out in the same manner as in Example 5 except that the reaction time was changed to 24 hours, the acetaldehyde capture rate was 99.9% even after expiration of 24 hours, and thus, the aldehyde scavenger of the present invention maintained a high aldehyde capture performance even after the lapse of a long period of time.

Examples 28 to 33 (Aldehyde Capture Test in a Gas Phase)

The aldehyde scavenger 0.5 mL prepared in each of Example 5 to 7 was dropwise added to 5 A filter paper (diameter 7 cm) manufactured by Advantech Co. and dried at 60° C. for 1 hour. This filter paper was sealed in a Tedlar bag and subjected to deaeration under reduced pressure, whereupon an aldehyde gas of 100 ppm (volume concentration) was injected in an amount of 1 L. After being left to stand at room temperature for 1 hour, the gas in the Tedlar bag was permitted to be adsorbed on a cartridge (product name: Presep-C DNPH, manufactured by Wako Pure Chemical Industries, Ltd.) supporting 2,4-dinitrophenyl hydrazine (DNPH). From this cartridge, a DNPH-aldehyde condensate was eluted (eluent=acetonitrile), and the DNPH-aldehyde condensate in the eluate was quantified by liquid chromatograph (device name: Agilent 1220 Infinity LC, manufactured by Agilent Technologies, Inc.), whereupon the residual aldehyde concentration was calculated.

Comparative Examples 4 to 9

The operation was carried out in the same manner as in Examples 28 to 33 except that in place of the O-substituted mono hydroxylamine, Chem catch H-6000HS (hydrazide type, manufactured by Otsuka Chemical Co., Ltd.), piperazine (amine type) or glycine (amino acid-type) as a conventional product, was used.

Figure 2:
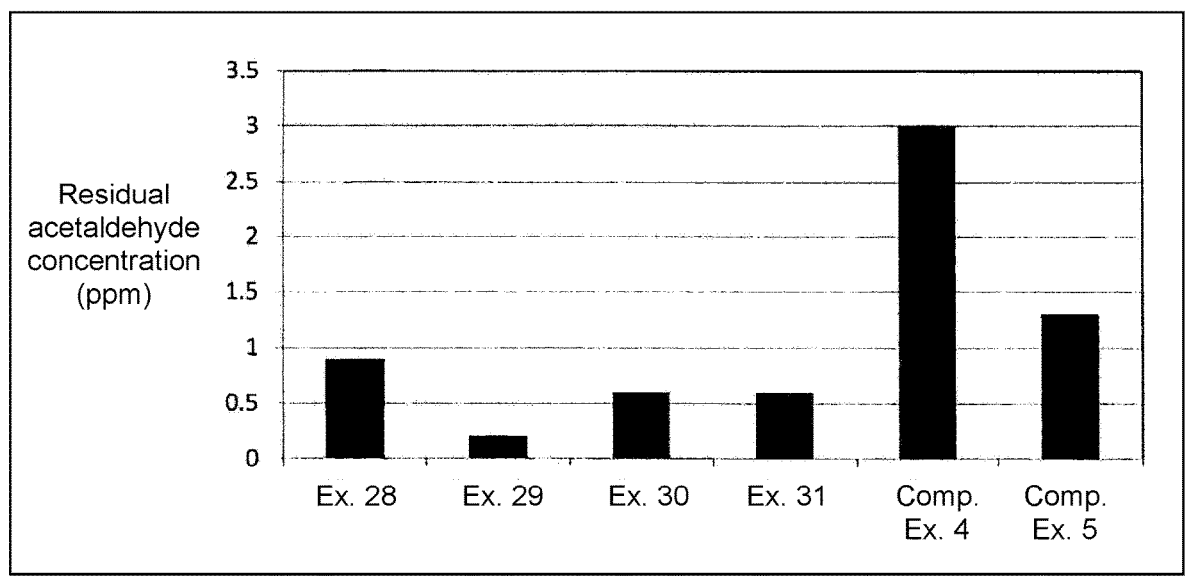
FIG. 2 is a diagram showing the residual acetaldehyde concentrations in Examples 28 to 31 and Comparative Examples 4 and 5.
Figure 3:
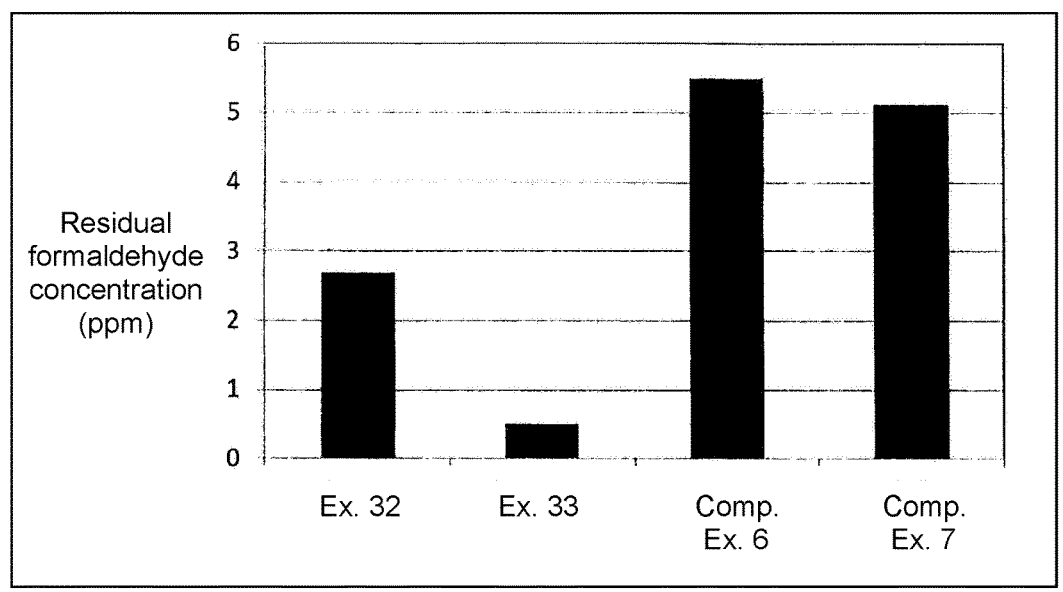
FIG. 3 is a diagram showing the residual formaldehyde concentrations in Examples 32 and 33 and Comparative Examples 6 and 7.

The results in Examples 28 to 33 and Comparative Examples 4 to 9 are shown in Table 3, and FIG. 2 and FIG. 3.

aldehyde gas of 100 ppm (volume concentration) was injected in an amount of 1 L. After being left to stand at room temperature for 1 hour, the gas in the Tedlar bag was quantified in the same manner as in Example 28 to 33, whereby the residual aldehyde concentration was 0.1 ppm.

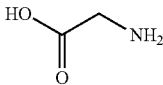

TABLE 3

Example 34

As a result of the operation carried out in the same manner as in Example 28 except that the standing time at room temperature was changed to be 24 hours, the residual acetaldehyde concentration was decreased from 0.9 ppm (standing time: 1 hour) to 0.2 ppm, and thus, the aldehyde scavenger of the present invention maintained a high aldehyde capturing performance even after lapse of a long time.

Example 35

To the aldehyde scavenger prepared in Example 5, silica gel (PSQ60B, manufactured by Fuji Silysia Chemical Ltd.) was added, and water was distilled off under reduced pressure and dried at 60° C. for 1 hour (alkoxyamine supported amount=3 wt %). This powder 0.1 g was sealed in a Tedlar bag and deaerated under reduced pressure, whereupon an

Comparative Example 10

As a result of the operation carried out in the same manner as in Example 35 except that only the silica gel was used as the scavenger, the residual aldehyde concentration was 50.2 ppm.

As evident from Table 3, FIGS. 2 and 3, Example 35 and Comparative Example 10, the aldehyde scavengers of the present invention showed a high aldehyde capture performance as compared to the conventional scavengers even in the gas phase.

Example 36 (Test to Capture Aldehydes Derived from a Particle Board)

To a particle board (vertical 10 cm, horizontal 10 cm, thickness 1 cm), an aqueous solution of the scavenger containing 10 wt % of (aminooxy) acetic acid hemihydrochloride was applied at a rate of 22.2 g/m² and dried at room temperature for 24 hours. This particle board was sealed in a Tedlar bag together with air 1 L and left to stand at 60° C. for 1 hour, whereupon the gas in the Tedlar bag was quantified in the same manner as in Examples 28 to 33, whereby the acetaldehyde concentration was 0.6 ppm, and the formaldehyde concentration was 0.1 ppm.

Comparative Example 11

As a result of the operation carried out in the same manner as in Example 36 except that no scavenger was used, in the Tedlar bag, the acetaldehyde concentration was 14.9 ppm, and the formaldehyde concentration was 0.6 ppm.

Example 37 (Test to Capture Aldehydes Derived from a Urethane Foam)

To a urethane foam (vertical 4 cm, horizontal 5 cm, thickness 4 cm), an aqueous solution of the scavenger containing 5 wt % of (aminooxy) acetic acid was applied at a rate of 22.2 g/m² and dried at room temperature for 24 hours. This urethane foam was sealed in a Tedlar bag together with air 1 L and left to stand at 65° C. for 2 hours, whereupon the gas in the Tedlar bag was quantified in the same manner as in Examples 28 to 33, whereby the acetaldehyde concentration was less than 0.1 ppm, and the formaldehyde concentration was 0.1 ppm.

Comparative Example 12

As a result of the operation carried out in the same manner as in Example 37 except that no scavenger was used, in the Tedlar bag, the acetaldehyde concentration was 0.3 ppm, and the formaldehyde concentration was 0.8 ppm.

Comparative Example 13

As a result of the operation carried out in the same manner as in Example 37 except that as the scavenger, in place of the (aminooxy) acetic acid aqueous solution, a Chem catch H-6000HS (manufactured by Otsuka Chemical Co., Ltd.) aqueous solution was used, in the Tedlar bag, the acetaldehyde concentration was 0.3 ppm, and the formaldehyde concentration was 0.2 ppm.

As evident from Examples 36 to 37 and Comparative Examples 11 to 13, by applying the aldehyde scavenger of the present invention to an aldehyde generation source such as the particle board or urethane foam, it is possible to reduce the aldehyde generation amount, and it showed an excellent aldehyde capturing effect as compared to the conventional aldehyde scavenger.

Examples 38 to 45

The O-substituted polyhydroxylamine (0.23 mmol) was dissolved in water (5 mL), to prepare an aldehyde scavenger. Thereto, an aqueous solution 5 mL containing acetaldehyde (0.23 mmol) and diethylene glycol diethyl ether (0.2 wt %) as the internal standard substance, was mixed. After 1 minute, after 5 minutes, after 10 minutes and after 30 minutes, a portion (0.2 mL) of the reaction liquid was withdrawn, and thereto, sodium borohydride 1 mg was added to reduce the remaining acetaldehyde to ethanol. This solution was analyzed by gas chromatograph (GC-2014, manufactured by Shimadzu Corporation), and the residual acetaldehyde concentration was calculated from the area ratio of ethanol and diethylene glycol diethyl ether. Further, the aldehyde capture rate was also calculated from the above formula.

Comparative Examples 14 to 16

The operation was carried out in the same manner as in Examples 38 to 45 except that in place of the O-substituted polyhydroxylamine, Chem catch H-6000HS (hydrazide type, manufactured by Otsuka Chemical Co., Ltd.), piperazine (amine type) or glycine (amino acid-type) as a conventional product was used.

Figure 4:
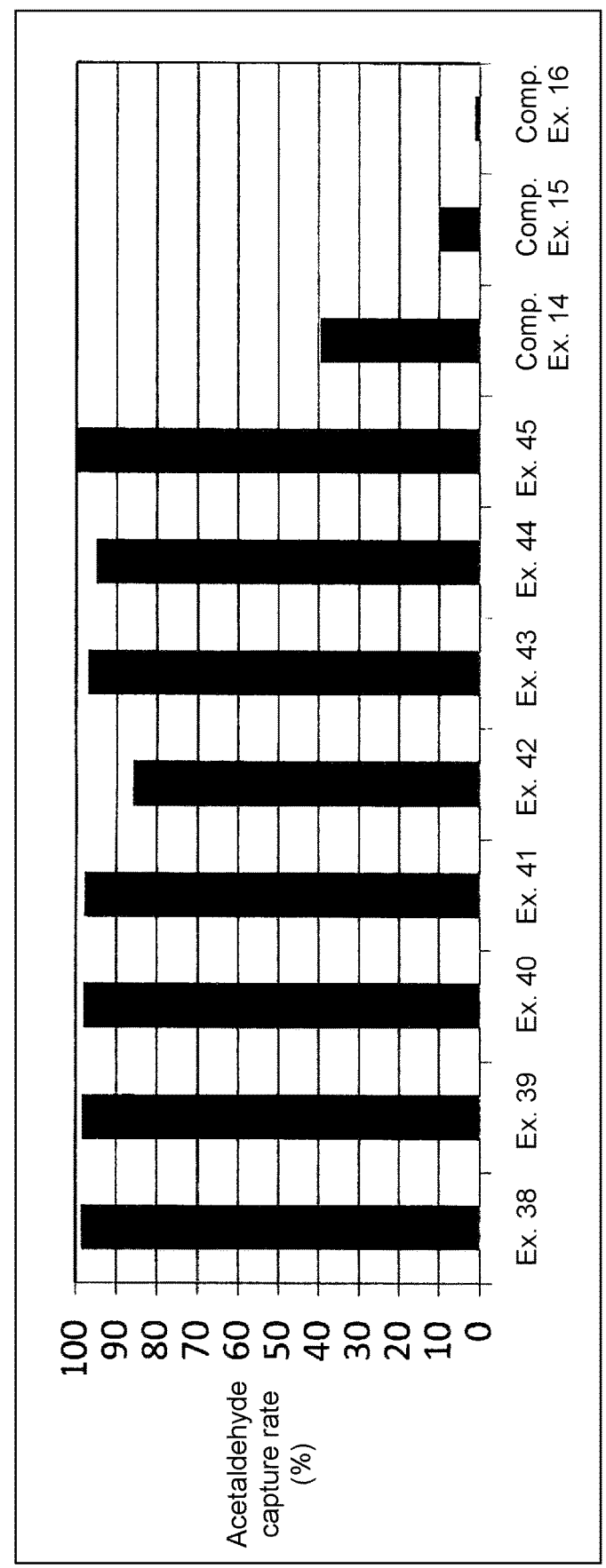
FIG. 4 is a diagram showing the acetaldehyde capture rates after 1 minute in Examples 38 to 45 and Comparative Examples 14 to 16.

The results (capture rates from after 1 minute to after 30 minutes) in Examples 38 to 45 and Comparative Examples 14 to 16 are shown in Table 4 and FIG. 4 (capture rate after 1 minute).

TABLE 4

|  | Ex. 38 | Ex. 39 | Ex. 40 |
| --- | --- | --- | --- |
|  | 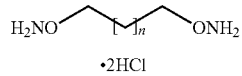 ·2HCl | | |
| Compound | n = 1 | n = 2 | n = 3 |
| Capture rate (%) after 1 min | 98.5 | 98.3 | 98.0 |
| Capture rate (%) after 5 min | 99.3 | 99.2 | 99.3 |
| Capture rate (%) after 10 min | 99.3 | 99.3 | 99.3 |
| Capture rate (%) after 30 min | 99.5 | 99.4 | 99.4 |

|  | Ex. 41 | Ex. 42 |
| --- | --- | --- |
|  | 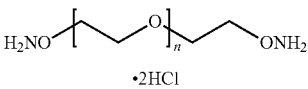 ·2HCl | |
| Compound | n = 1 | n = 2 |
| Capture rate (%) after 1 min | 97.8 | 85.8 |
| Capture rate (%) after 5 min | 98.9 | 85.9 |

TABLE 4-continued

| Capture rate (%) after 10 min | 99.0 | 85.9 |
|---|---|---|
| Capture rate (%) after 30 min | 99.0 | 86.3 |

| | Ex. 43 | Ex. 44 |
|---|---|---|
| Compound | 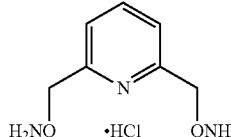 | 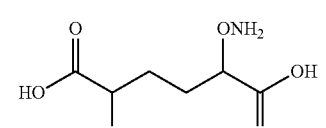 |
| Capture rate (%) after 1 min | 96.9 | 94.9 |
| Capture rate (%) after 5 min | 96.9 | 96.8 |
| Capture rate (%) after 10 min | 97.1 | 97.3 |
| Capture rate (%) after 30 min | 97.3 | 97.7 |

| | Ex. 45 | Comp Ex. 14 |
|---|---|---|
| Compound | 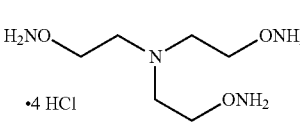 | Chem catch H-6000HS |
| Capture rate (%) after 1 min | 99.6 | 39.4 |
| Capture rate (%) after 5 min | >99.9 | 71.2 |
| Capture rate (%) after 10 min | >99.9 | 82.6 |
| Capture rate (%) after 30 min | >99.9 | 91.3 |

| | Comp. Ex. 15 | Comp. Ex. 16 |
|---|---|---|
| Compound | 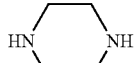 | 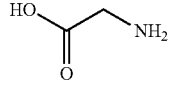 |
| Capture rate (%) after 1 min | 9.9 | 1.2 |
| Capture rate (%) after 5 min | 15.4 | 1.5 |
| Capture rate (%) after 10 min | 20.6 | 1.7 |
| Capture rate (%) after 30 min | 25.2 | 1.8 |

As evident from Table 4 and FIG. 4, the aldehyde scavengers of the present invention showed a high aldehyde capture performance as compared to the conventional scavengers.

Example 46

As a result of the operation carried out in the same manner as in Example 38 except that the aldehyde capture time was changed to 24 hours, the acetaldehyde capture rate was 99.9%, and thus, the aldehyde scavenger of the present invention maintained a high aldehyde capture performance even after lapse of a long time.

Example 47

Silica gel (PSQ60B manufactured by Fuji Silysia Chemical Ltd.) was added to the aldehyde scavenger prepared in Example 40 and, by distilling off water under reduced pressure, dried at 60° C. for 1 hour (alkoxyamine supported amount=3 wt %). This powder 0.1 g was sealed in a Tedlar bag and deaerated under reduced pressure, whereupon an aldehyde gas of 100 ppm (volume concentration) was injected in an amount of 1 L. After being left to stand at room temperature for 1 hour, the gas in the Tedlar bag was permitted to be adsorbed on a cartridge (product name: Presep-C DNPH, manufactured by Wako Pure Chemical Industries, Ltd.) supporting 2,4-dinitrophenyl hydrazine (DNPH). From this cartridge, a DNPH-aldehyde condensate was eluted (eluent=acetonitrile), and the DNPH-aldehyde condensate in the eluate was quantified by liquid chromatograph (device name: Agilent 1220 Infinity LC, manufactured by Agilent Technologies, Inc.), whereby the residual aldehyde concentration was 0.4 ppm.

Comparative Example 17

As a result of the operation carried out in the same manner as in Example 47 except that only the silica gel was used as the scavenger, the residual aldehyde concentration was 50.2 ppm.

As evident from Example 47 and Comparative Example 17, the aldehyde scavenger of the present invention showed a high aldehyde capture performance as compared to the conventional scavenger even in the gas phase.

INDUSTRIAL APPLICABILITY

The aldehyde scavenger and the method for removing aldehydes of the present invention will capture aldehydes quickly and continuously. As a result, it is possible to reduce aldehydes harmful to the human bodies and to improve the human living environment.

The entire disclosures of Japanese Patent Application No. 2016-254724 filed on Dec. 28, 2016, Japanese Patent Application No. 2016-254725 filed on Dec. 28, 2016, Japanese Patent Application No. 2017-245500 filed on Dec. 21, 2017 and Japanese Patent Application No. 2017-245501 filed on Dec. 21, 2017 including specifications, claims, drawings and summaries are incorporated herein by reference in their entireties.

The invention claimed is:

1. A method for removing aldehydes, comprising:
bringing an aldehyde scavenger into contact with an aldehyde generation source to remove the aldehydes,
wherein the aldehyde scavenger includes at least one O-substituted hydroxylamine, or at least one chemically acceptable salt of the O-substituted hydroxylamine, and the chemically acceptable salt is at least one of a hydrochloride, a hydrobromide, a perchlorate, a silicate, a tetrafluoroborate, a hexafluorophosphate, a sulfate, a nitrate, a phosphate, an acetate, a citrate, a fumarate, a maleate, a trifluoromethanesulfonate, a trifluoroacetate, a benzoate, and a p-toluenesulfonic acid salt,
wherein the O-substituted hydroxylamine has formula (1)

$$R^1-ONH_2 \quad (1)$$

where $R^1$ is a methyl group or an ethyl group which, at a chemically acceptable position, is substituted by at least a carboxy group and is optionally further substituted by a phenyl group.

2. The method of claim 1, wherein $R^1$ is one of a carboxymethyl group, a 1-carboxyethyl group, a 2-carboxyethyl group, an α-carboxy benzyl group, an α-carboxy-phenethyl group, and a β-carboxy-phenethyl group.

3. The method of claim 1, wherein $R^1$ is a carboxymethyl group.

4. The method of claim 1, wherein the aldehyde scavenger is included in an aqueous solution and brought into contact with the aldehyde generation source.

5. The method of claim 2, wherein the aldehyde scavenger is included in an aqueous solution and brought into contact with the aldehyde generation source.

6. The method of claim 3, wherein the aldehyde scavenger is included in an aqueous solution and brought into contact with the aldehyde generation source.

7. The method of claim 4, wherein a content of the aldehyde scavenger included in an aqueous solution is within a range of from 1 to 50 wt %.

8. The method of claim 5, wherein a content of the aldehyde scavenger included in an aqueous solution is within a range of from 1 to 50 wt %.

9. The method of claim 6, wherein a content of the aldehyde scavenger included in an aqueous solution is within a range of from 1 to 50 wt %.

10. The method of claim 1, wherein the aldehyde scavenger is supported on a carrier which is insoluble in water.

11. The method of claim 2, wherein the aldehyde scavenger is supported on a carrier which is insoluble in water.

12. The method of claim 3, wherein the aldehyde scavenger is supported on a carrier which is insoluble in water.

13. The method of claim 1, wherein the aldehyde scavenger is supported on a polymeric carrier or an inorganic carrier which are insoluble in water.

14. The method of claim 2, wherein the aldehyde scavenger is supported on a polymeric carrier or an inorganic carrier which are insoluble in water.

15. The method of claim 3, wherein the aldehyde scavenger is supported on a polymeric carrier or an inorganic carrier which are insoluble in water.

16. The method of claim 1, wherein the aldehyde generation source comprises a plywood or an automobile ceiling material.

* * * * *